(12) United States Patent
Levinson et al.

(10) Patent No.: US 6,479,545 B1
(45) Date of Patent: Nov. 12, 2002

(54) FORMULATION FOR MENOPAUSAL WOMEN

(75) Inventors: R. Saul Levinson, Chesterfield, MO (US); Marc S. Hermelin, Glendale, MO (US); Mitchell I. Kirschner, St. Louis, MO (US)

(73) Assignee: Drugtech Corporation, Wilmington, DE (US)

( * ) Notice: Subject to any disclaimer, the term of this patent is extended or adjusted under 35 U.S.C. 154(b) by 0 days.

(21) Appl. No.: 09/409,059

(22) Filed: Sep. 30, 1999

(51) Int. Cl.$^7$ .................. A61K 31/185; A61K 33/06; A61P 15/00
(52) U.S. Cl. .................. 514/560; 514/899; 424/484
(58) Field of Search .................. 514/899, 560, 514/258; 424/451, 464, 484

(56) References Cited

U.S. PATENT DOCUMENTS

| 4,710,387 A | * | 12/1987 | Viterwaal et al. |
| 4,758,592 A |   | 7/1988  | Horrobin et al. |
| 4,900,734 A |   | 2/1990  | Maxon et al. |
| 4,945,103 A |   | 7/1990  | Cohen |
| 5,380,757 A |   | 1/1995  | Horrobin |
| 5,415,879 A | * | 5/1995  | Ort |
| 5,461,170 A |   | 10/1995 | Miyamoto et al. |
| 5,514,382 A |   | 5/1996  | Sultenfuss |
| 5,569,459 A |   | 10/1996 | Shylankevich |
| 5,855,949 A | * | 1/1999  | McClean |
| 5,922,704 A | * | 7/1999  | Bland |

OTHER PUBLICATIONS

*The Merck Manual* 1793–1794 (16$^{th}$ Ed. 1992).
*Physicians' Desk Reference for Nonprescription Drugs*, (9$^{th}$ Ed., 1988) 718.

* cited by examiner

Primary Examiner—Edward J. Webman
(74) Attorney, Agent, or Firm—Nath & Associates PLLC; Gary M. Nath; Joshua B. Goldberg

(57) ABSTRACT

The present disclosure relates to novel compositions which provide improved nutritional support for premenopausal and menopausal women and/or relief from symptoms associated with menopause, as well as prophylactic effects, and methods for using same.

10 Claims, No Drawings

FORMULATION FOR MENOPAUSAL WOMEN

BACKGROUND OF THE INVENTION

1. Field of the Invention

The present invention is directed to novel compositions for use by premenopausal women and menopausal women for the purpose of providing improved nutritional support and/or relief from the symptoms of menopause, as well as to methods for using same.

2. Description of the Related Art

Menopause, the transition from the reproductive stage to the non-reproductive stage of a woman's life, is characterized primarily by the cessation of menstruation. However, menopause has come to signify much more than simply the loss of reproductive capability, as it is also associated with a number of acute and chronic conditions. Menopausal syndrome consists of a number of varying and often highly distressing symptoms resulting from hormonal imbalance and nutritional deficiency in the female body.

Hot flashes and sweating secondary to vasomotor instability affect 75% of women. Psychologic and emotional symptoms of fatigue, insomnia, irritability and nervousness are common. Lack of sleep due to disturbance by recurring hot flashes contributes to fatigue and irritability. Dizziness, parenthesis and cardiac symptoms of palpitations and tachycardia may also occur; the incidence of heart disease increases. Other common symptoms include nausea, constipation, diarrhea, arthralgia and myalgia. *The Merck Manual*, 1793 (16$^{th}$ Ed. 1992).

Menopause is also characterized by osteoporosis, or loss of bone density, resulting in increased bone fractures and vertebral column collapse. Bone loss begins around age 35. This loss accelerates during menopause, which generally occurs around age 45 to 55. Bone mass losses average 1–2% each year after menopause. Primary sites are the vertebrae, which show anterior collapse resulting in stooping and backache, the hips and the wrist. *The Merck Manual* 1793 (16$^{th}$ Ed. 1992). Osteoporosis develops over decades and is related to peak bone mass, as well as to the degree of bone loss.

Estrogen replacement therapy has been used to relieve the symptoms of menopause. *The Merck Manual* 1793(16$^{th}$ Ed. 1992). However, estrogen therapy is not without its limitations. In some instances the side effects of estrogen therapy can be quite severe. These side effects include increased risk of certain cancers, such as breast cancer. Estrogen has also been implicated in certain endometrial cancers. Although treatments with progestin have been shown to counter these adverse side effects, postmenopausal women treated with such an estrogen-progestin regimen frequently experience undesirable uterine bleeding. Further, hormone therapy alone is insufficient to meet the varied and heightened nutritional requirements of a woman during this phase in her life. Adequate nutritional intake is also necessary.

Appropriate nutritional intake is increasingly important to menopausal women. For example, adequate calcium intake prevents osteoporosis. Moreover, certain vitamins and minerals enhance calcium absorption and utilization. However, while vitamin and mineral supplements providing calcium for women is known in the art, conventional supplements fail to meet other nutritional requirements of menopausal women. Specifically, conventional supplements lack certain fatty acids which are especially useful to treat symptoms of fatigue or tiredness commonly experienced by a woman undergoing menopause. Fatty acids are essential in supporting life's activities as the body derives most of its energy from triglycerides, a molecule of glycerol with three fatty acids. Linoleic acid and linolenic acid, in particular, are two fatty acids which are indispensable to body functions. The inclusion of these two fatty acids in nutritional supplements is of particular significance because they are not produced by the body and must be supplied through food. However, conventional nutritional supplements fail to include these two fatty acids.

The use of fatty acids in various forms and for various purposes has been previously disclosed. Horrobin et al. disclose a method of prevention or treatment of endometriosis wherein effective amounts of one or both gamma-linolenic acid and/or dihomo-gamma-linolenic acid are administered to women. Specifically, the fatty acids may be administered in the form of the acid itself or as an ester, amide, salt or any other functional derivative capable of being converted to the acid within the body and may be from natural or synthetic sources.

Maxson et al., U.S. Pat. No. 4,900,734, disclose a pharmaceutical composition containing estradiol and progesterone for oral administration. Specifically, the pharmaceutical composition comprises estradiol dissolved in an oil vehicle containing a suspension of micronized progesterone. Further, the oil vehicle is high in glycerides of polyunsaturated fatty acids. Specifically, linoleic and linolenic acids are disclosed as particularly effective polyunsaturated fatty acids. The combined administration of these steroids is disclosed as being useful for replacement hormone therapy in the treatment of menopausal women.

Cohen, U.S. Pat. No. 4,945,103, discloses a method for treating women who suffer from premenstrual syndrome (PMS) which comprises administration of melatonin in sufficient doses to relieve symptoms associated with PMS. Specifically, Cohen discloses that progestogen can be administered in combination with melatonin. Further, melatonin can be administered to women orally, parenterally or in the form of an implant. Cohen specifically discloses that PMS may be linked to a nutritional deficiency in either vitamin B-complex, especially vitamin B6 (pyroxidine), or essential fatty acids, especially linolenic acid.

Horrobin, U.S. Pat. No. 5,380,757, discloses a method of treatment of vulvar dystrophy and/or vaginal dryness, which medicament comprises gamma-linolenic (GIA) and/or dihomo-gamma-linolenic acid (DGIA), optionally in association with other essential fatty acids of the n-6 or n-3 series. Horrobin discloses that deficiency of linoleic acid in the diet may produce atrophy and hyperkeratosis of the skin.

Miyamoto et al., U.S. Pat. No. 5,461,170, disclose a glyceride preparation having a branched saturated fatty acid and/or myristic acid residues for use in liquid oils and/or solid cosmetics of the same. Specifically, Miyamoto et al. disclose a polyol fatty-acid ester having mixed acid group produced by reacting a partial ester of a polyol and a branched fatty acid with a straight chain fatty acid or a lower alcohol ester thereof in the presence of a lipase. The obtained glyceride mixture contains a large amount of diglyceride having a branched, saturated fatty acid group and a straight chain, fatty acid group. The reference does not specifically disclose either linoleic or linolenic acid and/or menopause.

Sultenfuss, U.S. Pat. No. 5,514,382, discloses a daily vitamin and mineral supplement for women comprising vitamin A, beta-carotene, niacin, riboflavin, pantothenic acid, pyridoxine, cyanocobalamin, biotin, paraaminobenzoic acid, inositol, choline, calcium, chromium, copper, iodine, iron, magnesium, manganese, molybdenum, selenium, zinc, and bioflavonoid. For women over 40 years of age, iron is optionally included.

Shylankevich, U.S. Pat. No. 5,569,459, discloses compositions containing various vitamins, minerals and herbal extracts that can be used for alleviation of premenstrual syndrome, menopausal disorders, and stimulating estrogen production. Specifically, the invention relates to such pharmaceutical compositions and dietary supplements that contain natural soybean phytoestrogens of the isoflavone group.

Vitamins For Women disclose a Calcium/Vitamin/Mineral supplement program for women over forty. Specifically, the "over forty" formula discloses a composition containing ingredients which come in day and/or night formulas that "assure better utilization and absorption." *Physicians's Desk Reference for Nonprescription Drugs*, (9th Ed., 1988) 718.

However, the previously disclosed formulations are deficient for various reasons. In particular, none of the previously disclosed formulations contain critical components, such as essential fatty acids or calcium, in amounts specifically tailored to meet the needs of premenopausal and menopausal women. Moreover, the previously disclosed formulations fail to disclose the significance of the proportion of the various components to one another. Therefore, there is a need for formulations specifically tailored to meet the needs of menopausal women. Further, there is a need for drug delivery regimens which are specifically adapted to meet the needs of premenopausal and menopausal women.

SUMMARY OF THE INVENTION

The compositions of the present inventive subject matter overcome the deficiencies of currently-available nutritional supplements by providing formulations and drug delivery regimens which are specifically tailored for women just prior to, during and after the period of menopause. The present compositions contain a novel combination of various components, such as fatty acids, in critical ratios and amounts, optionally in combination with various vitamins and minerals.

One embodiment of the present inventive subject matter is a composition for administration to a menopausal woman, which comprises:
- an essential fatty acid compound selected from the group consisting of a linoleic acid compound, a linolenic acid compound, a docosahexaenoic acid compound, an omega-3 fatty acid compound, an omega-2 fatty acid compound, a derivative thereof and a combination thereof in an amount of about 10 mg to about 1,000 mg;
- a calcium compound or derivative thereof in an amount of about 400 mg to about 2500 mg;
- a folic acid compound or derivative thereof in an amount of about 0.4 mg to about 5.0 mg; and
- wherein the weight ratio of the essential fatty acid compound to the calcium compound or derivative thereof is about 1:0.4 to 250 in a single or multiple dosage unit.

Another embodiment of the present inventive subject matter is a composition for administration to a menopausal woman, which comprises:
- a first fatty acid compound selected from the group consisting of a linoleic acid compound, a derivative thereof and a combination thereof in an amount of about 10 mg to about 1,000 mg;
- a second fatty acid compound selected from the group consisting of a linolenic acid compound, a derivative thereof and combinations thereof in an amount of about 10 mg to about 1,000 mg;
- a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;
- a calcium compound or derivative thereof in an amount of about 400 mg to about 2500 mg;
- a folic acid compound or derivative thereof in an amount of about 0.4 mg to about 5.0 mg;
- wherein the weight ratio of the sum of the amounts of said first and second fatty acid compounds to the amount of said third fatty acid compound is about 1:0.5 to 1.5; and
- wherein the weight ratio of the sum of the amounts of said first, second and third fatty acid compounds to the amount of said calcium compound or derivative thereof is about 1:0.4 to 50.

A further embodiment of the present inventive subject matter is a composition for administration to a menopausal woman, which comprises:
- a first fatty acid compound selected from the group consisting of a linoleic acid compound, a derivative thereof and a combination thereof in an amount of about 10 mg to about 1,000 mg;
- a second fatty acid compound selected from the group consisting of a linolenic acid compound, a derivative thereof and combinations thereof in an amount of about 10 mg to about 1,000 mg;
- a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;
- a calcium compound or derivative thereof in an amount of about 400 mg to about 2500 mg;
- a folic acid compound or derivative thereof in an amount of about 0.4 mg to about 5.0 mg;
- a vitamin C compound or derivative thereof in an amount of about 25 mg to about 500 mg;
- a vitamin E compound or derivative thereof in an amount of about 10 mg to about 500 mg;
- wherein the weight ratio of the sum of the amounts of said first and second fatty acid compounds to the amount of said third fatty acid compound is about 1:0.5 to 1.5; and
- wherein the weight ratio of the sum of the amounts of said first, second and third fatty acid compounds to the amount of said calcium compound or derivative thereof is about 1:0.4 to 50.

An even further embodiment of the present inventive subject matter is a composition for administration to a menopausal woman, which comprises:
- a first fatty acid compound selected from the group consisting of a linoleic acid compound, a derivative thereof and a combination thereof in an amount of about 10 mg to about 1,000 mg;
- a second fatty acid compound selected from the group consisting of a linolenic acid compound, a derivative thereof and combinations thereof in an amount of about 10 mg to about 1,000 mg;
- a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;

a calcium compound or derivative thereof in an amount of about 400 mg to about 2500 mg;

a folic acid compound or derivative thereof in an amount of about 0.4 mg to about 5.0 mg;

a vitamin C compound or derivative thereof in an amount of about 25 mg to about 500 mg;

a vitamin E compound or derivative thereof in an amount of about 10 mg to about 500 mg;

a vitamin A compound or derivative thereof in an amount of about 2,500 IU to about 6,500 IU;

wherein the weight ratio of the sum of the amounts of said first and second fatty acid compounds to the amount of said third fatty acid compound is about 1:0.5 to 1.5; and wherein the weight ratio of the sum of said first, second and third fatty acid compounds to the amount of said calcium compound or derivative thereof is about 1:0.4 to 50.

Another embodiment of the present inventive subject matter is a composition for administration to a menopausal woman, which comprises:

a first fatty acid compound selected from the group consisting of a linoleic acid compound, a derivative thereof and a combination thereof in an amount of about 10 mg to about 1,000 mg;

a second fatty acid compound selected from the group consisting of a linolenic acid compound, a derivative thereof and combinations thereof in an amount of about 10 mg to about 1,000 mg;

a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;

a calcium compound or derivative thereof in an amount of about 400 mg to about 2500 mg;

a folic acid compound or derivative thereof in an amount of about 0.4 mg to about 5.0 mg;

a vitamin C compound or ester derivative thereof in an amount of about 25 mg to about 500 mg;

a vitamin E compound or derivative thereof in an amount of about 10 mg to about 500 mg;

a vitamin B6 compound or derivative thereof in an amount of about 10 mg to about 50 mg;

a vitamin B12 compound or derivative thereof in an amount of about 25 mcg to about 75 mcg;

a vitamin D compound or derivative thereof in an amount of about 200 IU to about 625 IU;

wherein the weight ratio-of the sum of the amounts of said first and second fatty acid compounds to the amount of said third fatty acid compound is about 1:0.5 to 1.5; and wherein the weight ratio of the sum of the amounts of said first, second and third fatty acid compounds to the amount of said calcium compound or derivative thereof is about 1:0.4 to 50.

Yet another embodiment of the present inventive subject matter is a composition for administration to a menopausal woman, which comprises:

a biologically active substance for treating symptoms of menopause;

a calcium compound or derivative thereof in an amount of about 400 mg to about 2500 mg;

a folic acid compound or derivative thereof in an amount of about 0.4 mg to about 5.0 mg.

A further embodiment of the present inventive subject matter is a drug delivery regimen, which comprises:

a first dosage form comprising a first biologically active substance to be administered to a menopausal woman at a predetermined time period;

a second dosage form comprising a second biologically active substance to be administered to the menopausal woman simultaneously with said first dosage form;

wherein said first biologically active substance and said second biologically active substance are incompatible substances.

An additional embodiment of the present inventive subject matter is a method for providing nutritional supplementation to a menopausal woman, which comprises:

administering an essential fatty acid compound to the woman during the period commencing at the onset of menopause, said essential fatty acid compound being selected from the group consisting of a linoleic acid compound, a linolenic acid compound, a docosahexaenoic acid compound, an omega-3 fatty acid compound, an omega-2 fatty acid compound, a derivative thereof and a combination thereof;

administering about 400 mg to about 2500 mg of a calcium compound or derivative thereof to the woman during the period commencing at the onset of menopause;

administering about 0.4 mg to about 5.0 mg of a folic acid compound or derivative thereof to the woman during the period commencing at the onset of menopause; and wherein the weight ratio of the essential fatty acid compound to the calcium compound or derivative thereof is about 1:0.4 to 250.

Another embodiment of the present inventive subject matter is a method for providing nutritional supplementation to a menopausal woman, which comprises:

administering a first fatty acid compound to the woman during a period commencing at the onset of menopause, said first fatty acid compound being selected from the group consisting of a linoleic acid compound, a derivative thereof and a combination thereof;

administering a second fatty acid compound to said woman during the period commencing at the onset of menopause, said second fatty acid compound being selected from the group consisting of a linolenic acid compound, a derivative thereof and a combination thereof;

administering a third fatty acid compound to said woman during the period commencing at the onset of menopause, said third fatty acid compound being selected from the group consisting of a docosahexaenoic acid compound, an omega-3 fatty acid, an omega-2 fatty acid, a derivative thereof and a combination thereof, and said third fatty acid compound being provided to the woman together with said first and second fatty acid compounds;

administering about 400 mg to about 2500 mg of a calcium compound or derivative thereof to said woman;

wherein the weight ratio of the sum of the amounts of said first and second fatty acid compounds to the amount of said third fatty acid compound is about 1:0.5 to 1.5; and wherein the weight ratio of the sum of the amounts of said first, second and third fatty acid compound to the amount of said calcium compound or derivative thereof is about 1:0.4 to 50.

Yet another embodiment of the present inventive subject matter is a method for providing nutritional supplementation to a menopausal woman while reducing symptoms associated with menopause, which comprises:

administering a first fatty acid compound to the woman during a period commencing at the onset of menopause, said first fatty acid compound being selected from the group consisting of a linoleic acid compound, a derivative thereof and a combination thereof;

administering a second fatty acid compound to said woman during the period commencing at the onset of menopause, said second fatty acid compound being selected from the group consisting of a linolenic acid compound, a derivative thereof and a combination thereof;

administering a third fatty acid compound to said woman during the period commencing at the onset of menopause, said third fatty acid compound being selected from the group consisting of a docosahexaenoic acid compound, an omega-3 fatty acid, an omega-2 fatty acid, a derivative thereof and a combination thereof, and said third fatty acid compound being provided to the woman together with said first and second fatty acid compounds;

administering about 400 mg to 2500 mg of a compound or derivative thereof to said woman;

administering a therapeutic substance to said woman;

wherein the weight ratio of the sum of the amounts of said first and second fatty acid compounds to the amount of said third fatty acid compound is about 1:0.5 to 1.5; and wherein the weight ratio of the sum of said first, second and third fatty acid compound to the amount of said calcium compound or derivative thereof is about 1:0.4 to 50.

A further embodiment is a method for delaying the onset of menopause, which comprises: administering an essential fatty acid to a woman prior to menopause, said fatty acid being selected from the group consisting of a linoleic acid compound, a linolenic acid compound, a docosahexaenoic acid compound, an omega-3 fatty acid compound, an omega-2 fatty acid compound, a derivative thereof and a combination thereof; wherein said essential fatty acid is administered in an amount sufficient to delay the onset of menopause.

A still further embodiment is a method for providing nutritional supplementation to a menopausal woman while reducing symptoms associated with menopause, which comprises:

administering a fatty acid compound to the woman during a period commencing at the onset of menopause, said fatty acid compound being selected from the group consisting of a linoleic acid compound, a linolenic acid compound, a docosahexaenoic acid compound, an omega-3 fatty acid, an omega-2 fatty acid, a derivative thereof and a combination thereof;

administering about 400 mg to 2500 mg of a calcium compound or derivative thereof to said woman;

and administering a non-nutritional active to said woman.

Another embodiment is a method for reducing the possibility of premature menopause, which comprises: administering an essential fatty acid to a woman prior to menopause, said fatty acid being selected from the group consisting of a linoleic acid compound, a linolenic acid compound, a docosahexaenoic acid compound, an omega-3 fatty acid compound, an omega-2 fatty acid compound, a derivative thereof and a combination thereof; wherein said essential fatty acid is administered in an amount sufficient to reduce the risk of premature menopause.

An additional embodiment is a method for providing nutritional supplementation to a premenopausal woman or a menopausal woman, which comprises: administering to the premenopausal woman or menopausal woman a biologically active substance for treating symptoms of menopause; administering to the premenopausal woman or menopausal woman a calcium compound or derivative thereof in an amount of 400 mg to about 2500; and administering to the premenopausal woman or menopausal woman a folic acid compound or derivative thereof in an amount of about 0.4 mg to about 5.0 mg.

DETAILED DESCRIPTION OF THE INVENTION

As used herein, "menopausal woman" refers to any woman who has experienced ovarian failure. The ovarian failure can be measured by blood tests for low estrogen levels (estradiol) or elevated gonadotropin levels (follicle stimulating hormone). When menopause occurs it remains for the life of the woman. The term "menopause" also encompasses the postmenopause or the postmenopausal period. The term "menopause" also encompasses natural menopause and artificial menopause. "Premenopausal woman" refers to any woman during the period commencing five years prior to onset of menopause.

"Nutritional stores" refers to the levels of vitamins, minerals and other nutrients which will be available for use by the menopausal woman.

"Nutritional status" refers to the presence or absence of any nutrient deficiency, or in other words, the extent to which physiological nutrient demands are being satisfied such that deficiency is avoided.

"Optimize neurological development" refers to attainment of the highest degree of neurological development possible through natural processes without the use of any unnatural substances or procedures, such as drugs, surgery and the like.

"Biologically active substance" refers to any substance or substances comprising a drug, active therapeutic substance, metabolite, medicament, vitamin, or mineral, any substance used for treatment, prevention, diagnosis, cure or mitigation of disease or illness, any substance which affects anatomical structure or physiological function, or any substance which alters the impact of external influences on an animal, or metabolite thereof, and as used herein, encompasses the terms "active substance", "therapeutic substance", "agent", "active agent", "drug", "medication", "medicine", "medicant", and other such similar terms.

"Non-nutritional active" refers to any substance or substances comprising a drug, active therapeutic substance, metabolite, or medicament, or any other substance used for treatment, prevention, diagnosis, cure or mitigation of disease or illness, any substance which affects anatomical structure or physiological function, or any substance which alters the impact of external influences on an animal, or metabolite thereof, and as used herein, that is not a vitamin, mineral, or any other nutritional compound or compositions.

"Specific physiological needs" refers to the unique requirements for certain levels of certain nutrients by one class of persons, such as menopausal women, premenopausal women, postmenopausal women, etc., as distinguished from other classes.

"Biologically-acceptable" refers to being safe for human consumption.

"Storage-incompatible substances" refers to substances that may not be formulated together in a single dosage unit or stored together in direct contact because the substances will interact in a negative manner and also substances that cannot be formulated together in a single dosage unit because the sum total of the dosage amounts of the substances would result in a single dosage unit which is too large to be swallowed. The term also refers to substances which may be stored in direct contact, however, one of the substances is preferably formulated in a dosage form which is either not preferred or incompatible with the other substance. Storage-incompatibility also refers to two or more substances wherein at least one substance is a prescription substance and at least one substance is a non-prescription substance.

"Storage-incompatibility" refers to the state that exists between storage-incompatible substances, as defined above.

The compositions of the present inventive subject matter provide several specific new and unexpected benefits. First, the formulations ensure that menopausal women are provided with adequate energy during the period of menopause. Secondly, the formulations allow the menopausal women to maintain adequate fatty acid stores for both her future use. Thirdly, the fatty acids optimize the neurological maintenance of the menopausal women. Fourthly, when administered just prior to menopause, the present compositions prepare women for the increased physiological demands and stresses to be placed upon their bodies. Additionally, the present compositions provide nutritional supplementation to women during the early stage of menopause known as perimenopause. Finally, the present compositions help minimize the risk of menopause related disorders and symptoms resulting from such disorders.

The present inventive subject matter is based, in part, on the discovery that when compositions having certain fatty acids, in certain amounts and proportions to one another, are administered to women just prior to, during and after menopause, the women will achieve optimal nutritional supplementation. In particular, supplementing a menopausal woman's diet with the formulations described below for a period commencing when symptoms of menopause are actually experienced, or preferably just prior to when menopause would generally be expected, will ensure that the woman has adequate essential fatty acids for present and future use. The fatty acid supplement may also further contain vitamins and minerals to confer added health benefits to the menopausal woman. In addition to benefitting humans, the present invention can also benefit non-human mammals. The composition of the present invention could be administered to a mammal in animal feed, pill form, or other appropriate dosage forms to such mammals.

Without being limited by theory, the present compositions stimulate or play a vital role in one or more natural biological pathways. For example, the arachidonic acid cascade may play a significant role in the support and maintenance of a menopausal woman's health. Specifically, in the arachidonic acid cascade, linoleic acid is converted first to gamma-linolenic acid and then to further metabolites such as dihomo-gamma-linoleic acid and arachidonic acid which are precursors of 1 and 2 series prostaglandin respectively, as shown in the outline below:

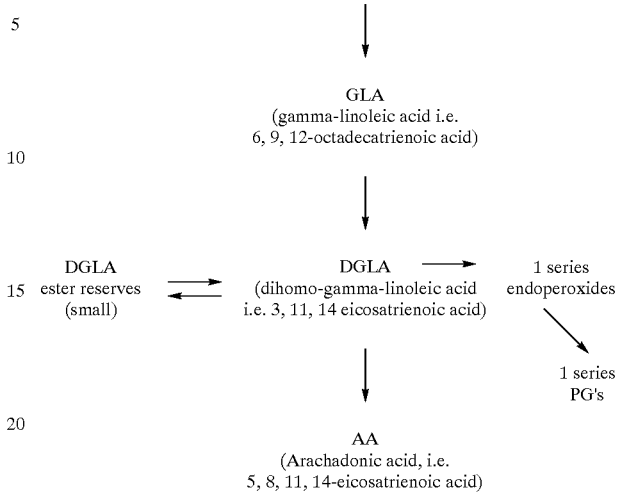

The present composition may contain an essential fatty acid compound. The fatty acid compound may be a linoleic acid compound, derivatives thereof or any combination of linoleic acid and/or linoleic acid derivatives. The fatty acid compound may be a linolenic acid compound, derivatives thereof and/or an combinations of linolenic acid and/or linoleic acid derivatives. The fatty acid compound may also be a docosahexaenoic acid compound, an omega-3 fatty acid compound, an omega-2 fatty acid compound, derivatives thereof or combinations thereof. The fatty acid may further be a combination of any of the above discussed fatty acids.

Preferably, the fatty acid compound is present in the composition in an amount ranging from about 10 mg to 1,000 mg. More preferably, the fatty acid compound is present in the composition in an amount ranging from about 15 mg to 200 mg, independently of the other fatty acid compounds. Even more preferably, the fatty acid compounds is present in the composition in an amount ranging from about 20 mg to about 100 mg, independently of the other fatty acid compounds. Most preferably, the fatty acid compound is present in the composition in an amount ranging from about 25 mg to 50 mg, independently of the other fatty acid compounds.

Three fatty acid compounds may be present in the present composition in critical proportions to one another. Preferably, the weight ratio of the sum of the amounts of said first and second fatty acid compounds to the amount of said third fatty acid compound is about 1:0.5 to 1.5. More preferably, the weight ratio of the sum of the amounts of said first and second fatty acid compounds to the amount of said third fatty acid compound is about 1:0.7 to 1.3. Even more preferably, the weight ratio of the sum of the amounts of said first and second fatty acid compounds to the amount of said third fatty acid compound is about 1:0.9 to 1.2. Most preferably, the weight ratio of the sum of the amounts of said first and second fatty acid compounds to the amount of said third fatty acid compound is about 1:0.9 to 1.1.

The compositions of the present invention may incorporate any compound that can react with an essential fatty acid to form a biochemically active compound. Preferably, the compound is a compound which fulfills a nutritional need, for example, without limitation, sphingomyelin, myelin, derivatives thereof and combinations thereof.

Particular classes of fatty acid compound derivatives used in the present invention, include, without limitation, phospholipid esters of linoleic acid, ethers of linoleic acid, sterolderivatives of linoleic acid, phospholipid esters of linolenic acid, ethers of linolenic acid, sterolderivatives of linolenic acid and combinations thereof.

Non-limiting exemplary fatty acid compounds used in the present invention, include, without limitation, phosphatidal choline esters of linoleic acid, phosphatidal ether of linoleic acid, sipolsterol ester of linoleic acid, phosphatidal choline esters of linolenic acid, phosphatidal ether of linolenic acid, sipolsterol ester of linolenic acid and combinations thereof.

The present composition contains a calcium compound, derivatives thereof or any combination of calcium compound and derivatives thereof. Preferably, the calcium is present in the composition in an amount ranging from about 400 mg to about 2,500 mg. More preferably, the calcium is present in the composition in an amount ranging from about 600 mg to about 1,800 mg. Even more preferably, the calcium is present in the composition in an amount ranging from about 800 mg to about 1600 mg. Most preferably, the calcium is present in the composition in an amount ranging from about 1,000 mg to about 1400 mg.

The proportion of total fatty acids to total calcium content in the present inventions is a critical feature.

Where three fatty acid compounds are present, preferably, the weight ratio of the sum of the amounts of the first, second and third fatty acid compounds to the amount of said calcium compound or derivative thereof is about 1:0.4 to 50. More preferably, the weight ratio of the sum of the amounts of the first, second and third fatty acid compounds to the amount of said calcium compound or derivative thereof is about 1:4 to 20. Even more preferably, the weight ratio of the sum of the amounts of the first, second and third fatty acid compounds to the amount of said calcium compound or derivative thereof is about 1:7 to 15. Most preferably, the weight ratio of the sum of the amounts of the first, second and third fatty acid compounds to the amount of said calcium compound or derivative thereof is about 1:10 to 14.

The fatty acids of the present inventive subject matter may be used as such or as biologically acceptable and physiologically equivalent derivatives as, for example, detailed later herein. Reference to any of the fatty acids including reference in the claims is to be taken as including reference to the acids when in the form of such derivatives. Equivalence is demonstrated by entry into the biosynthetic pathways of the body as evidenced by effects corresponding to those of the acids themselves or their natural glyceride esters. Thus, indirect identification of useful derivatives is by their having the valuable effect in the body of the fatty acid itself, but conversion, for example, of gamma-linolenic acid to dihomo-gamma-linolenic acid and on to arachidonic acid can be shown directly by gas chromatographic analysis of concentrations in blood, body fat, or other tissue by standard techniques, well known to persons of ordinary skill in the art to which the present inventive subject matter pertains.

Derivatives of linoleic acid, as used in the present inventive subject matter, include, without limitation, salts of linoleic acid, alkaline salts of linoleic acid, esters of linoleic acid and combinations thereof. Derivatives of linolenic acid, as used in the present inventive subject matter, include, without limitation, salts of linolenic acid, alkaline salts of linolenic acid, esters of linolenic acid and combinations thereof. The salts and alkaline salts herein refer to those regularly used organic or inorganic salts which are acceptable for pharmaceutical use. Non-limiting exemplary linolenic acids include gamma-linoleic acid and dihomo-gamma-linolenic acid.

The fatty acids of the present inventive subject matter may be from any source, including, without limitation, natural or synthetic oils, fats, waxes or combinations thereof. Moreover, the fatty acids herein may be derived, without limitation, from non-hydrogenated oils, partially hydrogenated oils, fully hydrogenated oils or combinations thereof. Non-limiting exemplary sources of fatty acids include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof. Specific non-limiting exemplary fish or marine oil sources include shellfish oil, tuna oil, mackerel oil, salmon oil, menhaden, anchovy, herring, trout, sardines or combinations thereof. Preferably, the source of the fatty acids is fish or marine oil, soybean oil or flaxseed oil.

Calcium compounds include, but are not limited to, any of the well known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like. Derivatives of calcium compounds, as used herein, include, without limitation, salts of calcium, alkaline salts of calcium, esters of calcium, and combinations thereof. The salts and alkaline salts herein refer to those regularly used organic or inorganic salts which are acceptable for pharmaceutical use. The calcium of the present composition may be from any source, without limitation.

Folic acid is also incorporated into the composition of the present inventive subject matter. Preferably, folic acid is present in an amount ranging from about 0.4 mg to about 5.0 mg. More preferably, folic acid is present in an amount ranging from about 0.6 mg to about 1.3 mg. Even more preferably, folic acid is present in an amount ranging from about 0.8 mg to about 1.2 mg. Most preferably, folic acid is present in an amount ranging from about 0.9 mg to about 1.1 mg.

The present composition may optionally contain additional vitamins and biologically-acceptable minerals. Non-limiting exemplary vitamins and biologically acceptable minerals and their derivatives thereof for inclusion in the present compositions include vitamin A, B vitamins, vitamin C, vitamin D, vitamin E, vitamin K, iron, calcium, magnesium, potassium, copper, chromium, zinc, molybdenum, iodine, boron, selenium, manganese, bioflavonoid, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof. Other nutritionally active compounds may also be present, including without limitation, fiber, carbohydrates, fats, proteins, amino acids, derivatives thereof and combinations thereof.

When vitamin C is present in the composition of the present inventive subject matter, it is preferably present in an amount ranging from about 10 mg to about 600 mg. More preferably, the vitamin C is present in an amount ranging from about 25 mg to about 500 mg. Even more preferably, the vitamin C is present in an immediate release form in an amount ranging from about 25 mg to about 50 mg. Most preferably, the vitamin C is present in a controlled release form in an amount ranging from about 250 mg to about 500 mg.

When vitamin E is present in the composition of the present inventive subject matter, it is preferably present in an amount ranging from about 5 mg to about 500 mg. More preferably, the vitamin E is present in an amount ranging from about 10 mg to about 400 mg. Even more preferably, the vitamin E is present in a controlled release form in an amount ranging from about 250 mg to about 400 mg. Most preferably, the vitamin E is present in an immediate release form in an amount ranging from about 10 mg to about 50 mg.

Vitamin B6 may also be present in the composition of the present inventive subject matter. Vitamin B6 is preferably present in an amount ranging from about 5 mg to about 200 mg. More preferably, vitamin B6 is present in an amount ranging from about 10 mg to about 50 mg. Even more preferably, vitamin B6 is present in an amount ranging from 15 mg to about 40 mg. Most preferably, vitamin B6 is present in a controlled release form in an amount ranging from 20 mg to about 30 mg.

Vitamin B12 may also be incorporated into the present composition. Preferably, the vitamin B12 is present in an amount ranging from about 25 mcg to about 75 mcg. More preferably, the vitamin B12 is present in an amount ranging from about 35 mcg to about 65 mcg. Even more preferably, the vitamin B12 is present in an amount ranging from about 40 mcg to about 60 mcg. Most preferably, the vitamin B12 is present in an amount ranging from about 45 mcg to about 55 mcg.

Vitamin D may also be incorporated into the present composition. Preferably, vitamin D is present in an amount ranging from about 200 IU to about 625 IU. More preferably, vitamin D is present in an amount ranging from about 300 IU to about 500 IU. Even more preferably, vitamin D is present in an amount ranging from about 350 IU to about 450 IU. Most preferably, vitamin D is present in an amount ranging from about 375 IU to about 425 IU.

Vitamin A may also be incorporated into the present composition. Preferably, vitamin A is present in the composition in an amount ranging from about 2,500 IU to about 6,500 IU. More preferably, vitamin A is present in the composition in an amount ranging from about 4,000 IU to about 6,000 IU. Even more preferably, vitamin A is present in the composition in an amount ranging from about 4,500 IU to about 5,500 IU. Most preferably, vitamin A is present in the composition in an amount ranging from about 4,750 IU to about 5,250 IU.

Magnesium, when present, is preferably in the composition of the present inventive subject matter in an amount ranging from about 25 mg to about 400 mg. More preferably, magnesium is present in the composition of the present inventive subject matter in an immediate release form in an amount ranging from about 25 mg to about 100 mg. Even more preferably, magnesium is present in the composition of the present inventive subject matter in a controlled release form in an amount ranging from about 100 mg to about 400 mg. Acceptable magnesium compounds which may be incorporated into the present inventive subject matter include, but are not limited to, magnesium stearate, magnesium carbonate, magnesium oxide, magnesium hydroxide and magnesium sulfate.

The composition of the present inventive subject matter may also include one or more biologically active substances or therapeutic substances, including, without limitation, hormones, steroids, fiber, estrogens, progestins, sedative-hypnotics, barbiturates, benzodiazepines, antidepressants, tranquilizers, sedatives, osteoporotics, anti-platelets, aminobisphosphonates, herbals, herbal derivatives, plant derivatives, phyto-chemical derivatives and combinations thereof.

If the non-nutritional active is a hormone, the hormone is administered in a dosage amount ranging from about 0.15 mg to about 11.25 mg. If the non-nutritional active is an osteoporotic, the osteoporotic is administered in a dosage amount ranging from about 2.5 mg to about 60 mg.

Non-limiting exemplary therapeutic substances include, medroxyprogesterone acetate, megestrol acetate, clonidine, norethindrone acetate, ethinyl estradiol, conjugated estrogen, natural estrogen, synthetic estrogen, estradiol, progesterone, clomiphene, clomiphene citrate, zuclomiphene, zuclomiphene citrate, enclomiphene, enclomiphene citrate, aspirin, calcitonin, alendronate, etidronate, pamidronate, clodronate, tiludronate, residronate, ibandronate and combinations thereof.

Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. Johnswort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof. Herbal derivatives, as used herein, refers to herbal extracts, and substances derived from plants and plant parts, such as leaves, flowers and roots, without limitation. Preferably, the herbal or herbal derivative is black cohosh, licorice, false unicorn, siberian ginseng, sarsaparilla, squaw vine, blessed thistle and combinations thereof.

Various additives may be incorporated into the present composition. Optional additives of the present composition include, without limitation, starches, sugars, fats, antioxidants, amino acids, proteins, nucleic acids, electrolytes, derivatives thereof or combinations thereof.

Non-limiting exemplary amino acids of the present inventive subject matter include histidine, isoleucine, leucine, lysine, methionine, phenylalanine, threonine, tryptophan, valine, alanine, arginine, asparagine, aspartic acid, cysteine, glutamic acid, glutamine, glycine, proline, serine, tyrosine, derivatives thereof, and combinations thereof. Preferably, the amino acid present is leucine, isoleucine, valine, derivatives thereof or combinations thereof.

The compositions, methods and drug delivery regimens of the present inventive subject matter may facilitate the simultaneous administration of storage-incompatible substances, particularly storage incompatible substances tailored to the needs of premenopausal and menopausal women. Storage-incompatible substances may be any substances that may not be formulated together in a single dosage unit or stored together in direct contact because the substances will interact in a negative manner and also substances that cannot be formulated together in a single dosage unit because the sum total of the dosage amounts of the substances would result in a single dosage unit which is too large to be swallowed. Storage-incompatible substances also include those substances which may be stored in direct contact, however, one of the substances is preferably formulated in a dosage form which is either not preferred or incompatible with the other substance. The storage-incompatible substances may include any storage-incompatible substances, without limitation.

For example, the storage incompatible substances may be hydrophobic compounds and hydrophilic compounds, olefinic compounds and non-olefinic compounds, pH sensitive compounds and non-pH sensitive compounds, substances requiring an anhydrous environment and substances requiring a non-anhydrous environment, acidic drugs and basic drugs, effervescent tablets and high water content drugs or dosage forms, gelatin capsules and aldehydes, quaternary ammonium compounds and anionic substances or any combination of the above.

Storage incompatible substances also include substances that cannot be formulated together in a single dosage unit because the sum total of the dosage amounts of the substances results in a single dosage unit too large to swallow. The compositions, methods and drug delivery regimens of the present inventive subject matter address this problem by separating the large dosage into multiple doses small enough to swallow comfortably, while keeping all of the substances and doses together in one package.

Non-limiting exemplary storage incompatible substances include, without limitation, ascorbic acid and aluminum hydroxide, ascorbic acid and sodium bicarbonate, citric acid and sodium carbonate, folic acid and calcium carbonate, activated charcoal and amyl nitrate, gelatin capsules and formaldehyde, gelatine capsules and gluteraldehyde, konicin chloride and soap, etylpyridinium chloride and sodium stearate, omega fatty acids and combinations thereof.

It is also possible in the nutritional composition of the present inventive subject matter for the dosage form to combine any forms of release well known to persons of ordinary skill in the art. These include, without limitation, immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is performed using well known procedures and techniques available to the ordinary artisan. Each of these specific techniques or procedures for obtaining the release characteristics does not constitute an inventive aspect of this inventive subject matter all of which procedures are well known to those of ordinary skill in the art. As used herein, a "controlled release form" means any form having at least one component formulated for controlled release. As used herein, "immediate release form" means any form having all its components formulated for immediate release.

Any biologically-acceptable dosage form well known to persons of ordinary skill in the art, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, animal feeds, cereals, yogurts, cereal coatings, foods, nutritive foods, functional foods and combinations thereof. The preparation of the above dosage forms are well known to persons of ordinary skill in the art.

The following procedures represent, without limitation, acceptable methods of preparing formulations falling within the scope of the inventive subject matter. For example, animal feed may be made by methods well known to persons of ordinary skill in the art. Animal feeds may be prepared by mixing the formulation with binding ingredients to form a plastic mass. The mass is then extruded under high pressure to form tubular (or "spaghetti-like") structures that are cut to pellet size and dried.

Quick dissolve tablets may be prepared, for example, without limitation, by mixing the formulation with agents such as sugars and cellulose derivatives, which promote dissolution or disintegration of the resultant tablet after oral administration, usually within 30 seconds.

Cereal coatings may be prepared, for example, without limitation, by passing the cereal formulation, after it has been formed into pellets, flakes, or other geometric shapes, under a precision spray coating device to deposit a film of active ingredients, plus excipients onto the surface of the formed elements. The units thus treated are then dried to form a cereal coating.

For example, health bars may be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example, without limitation, may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are well versed in the processes and the machinery used as the chewable dosage form is a very common dosage form in the pharmaceutical industry.

Film coated tablets, for example, without limitation, may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, or to mask an obnoxious odor or taste, or to improve the usual properties of an unsightly uncoated tablet.

Compressed tablets, for example, without limitation, may be prepared by mixing the formulation with excipients intended to add binding qualities to disintegration qualities. The mixture is either directly compressed or granulated then compressed using methods and machinery quite well known to those in the industry. The resultant compressed tablet dosage units are then packaged according to market need, i.e., unit dose, rolls, bulk bottles, blister packs, etc.

The present inventive subject matter contemplates nutritional compositions formulated for administration by any route, including without limitation, oral, buccal, sublingual, rectal, parenteral, topical, inhalational, injectable and transdermal. The physicochemical properties of nutritional compositions, their formulations, and the routes of administration are important in absorption. Absorption refers to the process of nutritional composition movement from the site of administration toward the systemic circulation. Most orally administered nutritional compositions are in the form of tablets or capsules primarily for convenience, economy, stability, and patient acceptance. They must disintegrate and dissolve before absorption can occur. Using the present inventive subject matter with any of the above routes of administration or dosage forms is performed using well known procedures and techniques available to the ordinary skilled artisan.

The present inventive subject matter contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers used in the dissolution modifying system are preferably previously dissolved in an organic solvent and added in solution form. Preferred plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluble hydrophobic substances, such as diethyl phthalate, diethyl sebacate and caster oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

The composition of the present inventive subject matter may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times. For example, without limitation, the amount of calcium in a morning dose is different from the amount of calcium in an evening dose.

The compositions of the present invention are intended for use by humans and other mammals. The dosages are adjusted according to body weight and thus may be set forth herein on a per body weight basis. For example, if the formula specifies a range of about 10–1000 mg for a 55 kg individual, that range would be adjusted for a 35 kg individual to about 6.3–63 mg (e.g., the lower range limit=(35 kg/55 kg)*10 mg=6.3 mg). Decimal amounts may be rounded to the nearest whole number. In the above manner the present compositions may thus be adapted to be suitable for any individual, including any mammal, regardless of its size.

The present composition is adapted to meet the specific physiological needs of a menopausal woman. For example, the formulations may focus on special nutritional needs of a menopausal woman that are not generally or adequately addressed in nutritional or dietary supplements, such as essential fatty acids, without limitation. The iron and calcium, when present, are provided in amounts to optimize nutritional benefit to the menopausal woman, while minimizing unpleasant side effects which may accompany overly large doses. The formulation can be further tailored based upon the specific needs, genetic predispositions or identified deficiencies of individual women, on either a generalized or case by case basis for greater specificity. Further, the composition may be specifically adapted for treating conditions associated with menopause or to maximize neurological maintenance of a menopausal woman. The composition may also be adapted for inhibiting loss in bone mass and preventing deficiency of essential fatty acids in menopausal women. Moreover, the present composition can be used as one component of a prescribed therapy.

The compositions of the inventive subject matter may be provided in a blister pack or other such pharmaceutical package, without limitation. Further, the compositions of the present inventive subject matter may further include or be accompanied by indicia allowing women to identify the compositions as products for menopausal women. The indicia may further additionally include an indication of the above specified time periods for using said compositions. For example, without limitation, the indicia may be time indicia indicating a specific or general time of day for administration of the composition, or the indicia may be a day indicia indicating a day of the week for administration of the composition.

The composition of the present invention may be used prior to and during menopause. Use of the compositions may commence at the onset of menopause. The composition of the present inventive subject matter is preferably administered during a period commencing no later than the appearance of the first symptoms associated with menopause and continuing throughout a woman's life. More preferably, the composition is administered during a period of time commencing just prior to menopause or just prior to any symptoms of menopause. The phrases "just prior to menopause" and "prior to any symptoms of menopause" are intended herein to include commencement of administration of compositions approximately one month to five years prior to an age generally identified with initiation of menopause.

Preferably, the commencement of administration of the composition is when the woman is thirty five to fifty years of age. More preferably, the commencement of administration is one month prior to the woman turning forty years of age. Even more preferably, the commencement of administration is one year prior to the woman turning forty years of age. Most preferably, the commencement of administration is five years prior to the woman turning forty years of age.

The present inventive subject matter includes a method for providing nutritional supplementation to a menopausal woman. The methods include administration of the present composition to women during a critical period. The critical period of administration is the period commencing just prior to menopause and continuing through the postmenopausal period of a woman's life.

The method of the present inventive subject matter may prevent or at least minimize fatty acid deficiency in menopausal women. The present method may also be used to prevent or treat symptoms associated with menopause. Further, the present method may inhibit the loss in bone mass commonly experienced by menopausal women. The present method may delay onset of menopause and/or reduce possibility of premature menopause.

The present methods may be carried out alone or in conjunction with a therapeutic therapy or regimen, without limitation. The therapeutic therapy or regimen may be for treating symptoms associated with menopause or may be entirely unrelated to menopause. For example, without limitation, the present method may be incorporated as part of hormonal or estrogen therapy, or in combination with dietary manipulation.

The foregoing is considered as illustrative only of the principles of the inventive subject matter. Further, since numerous modifications and changes will readily occur to those skilled in the art, it is not desired to limit the inventive subject matter to the exact construction and operation shown and described, and accordingly all suitable modifications and equivalents may be resorted to, falling within the scope of the inventive subject matter.

The following examples are illustrative of preferred embodiments of the inventive subject matter and are not to be construed as limiting the inventive subject matter thereto. All percentages are based on the percent by weight of the final delivery system or formulation prepared unless otherwise indicated and all totals equal 100% by weight.

EXAMPLES

Example 1

The following formulations are used to prepare compositions for administration to premenopausal and menopausal women:

| Component | Dose | Units |
| --- | --- | --- |
| Vitamin A (Beta Carotene) | 5,000 | I.U. |
| Vitamin D | 400 | I.U. |
| Vitamin E | 400 | I.U. |
| Vitamin C | 100 | mg. |
| Vitamin B1 | 20 | mg. |
| Vitamin B2 | 20 | mg. |
| Vitamin B6 | 25 | mg. |
| Vitamin B12 | 50 | mcg. |
| Vitamin B3 | 100 | mg. |
| Folic Acid | 1.0 | mg. |
| Calcium Carbonate | 1,200 | mg. |
| Copper | 2 | mg. |
| Zinc | 15 | mg. |
| Selenium | 65 | mcg. |
| DHA/Linolenic/Linoleic Acid | 50/25/25 | mg. |

It would be anticipated that upon administration of the above composition, an average normal menopausal woman would be expected to have reduced incidence of nutritional deficiency and reduced menopausal-related symptoms or disorders when compared to an average normal menopausal woman following a conventional nutritional regimen.

Example 2

The following compositions are for administration to premenopausal women and menopausal women in accordance with the regimen indicated below:

| Regimen | Component | Dose |
| --- | --- | --- |
| First Morning Tablet (orange): | Calcium Carbonate | 350 mg |
| | B Complex | 55 mg |
| Second Morning Tablet (white): | Calcium Carbonate | 350 mg |
| | Vitamin A | 3,000 IU |
| | Vitamin C | 100 IU |
| | Vitamin D | 400 IU |
| | Selenium | 65 mcg |
| | Zinc | 15 mg |
| | Copper | 2 mg |
| Evening Tablet | Calcium Carbonate | 350 mg |
| | B Complex | 110 mg |
| | Vitamin A | 2,000 IU |
| | Folic Acid | 1 mg |
| Evening Capsule | Vitamin E | 400 IU |
| | DHA | 50 mg |
| | Linolenic Acid | 25 mg |
| | Linoleic Acid | 25 mg |
| | Calcium Carbonate | 150 mg |

It would be anticipated that upon following the above regimen, an average normal menopausal woman would be expected to have reduced incidence of nutritional deficiency and reduced menopausal-related symptoms or disorders when compared to an average normal menopausal woman following a conventional nutritional regimen.

Example 3

A soft gelatin supplement in accordance with the compositions of Examples 1 and 2 above, may be prepared, by first combining mineral oil and soybean oil in a first vessel and blending it to form a uniform oil mixture, heating the oil mixture to 45 degrees Celsius, and then adding propylene glycol. In a second vessel preheated to 70 degrees Celsius, yellow beeswax and soybean oil are added and blended until a uniform wax mixture is formed. The wax mixture is cooled to 35 degrees Celsius and then added to the oil mixture. To this combined oil and wax mixture, folic acid, vitamin B₆, iron, magnesium, and calcium are then added and blended together to form a uniform biologically active mixture. The mixture is then cooled to 30 degrees Celsius to form a viscous biologically active core composition, after which time the composition is ready for encapsulation in a soft gelatin shell.

A soft gelatin shell is prepared by heating purified water in a suitable vessel and then adding gelatin. This water gelatin mixture is mixed until the gelatin is fully dissolved, and then glycerin, preservatives, one or more flavors, and one or more colorants are added. This gelatin mixture is blended well and cooled. The shells are then filled with the core composition and formed in accordance with soft gelatin techniques commonly used and well known to persons of skill in the art.

Example 4

The following compositions are for administration to premenopausal women and menopausal women in accordance with the regimen indicated below:

| Regimen | Component | Dose |
| --- | --- | --- |
| First Morning Tablet (orange): | Calcium Carbonate | 350 mg |
| | B Complex | 55 mg |
| Second Morning Tablet (white): | Calcium Carbonate | 350 mg |
| | Vitamin A | 3,000 IU |
| | Vitamin C | 100 IU |
| | Vitamin D | 400 IU |
| | Selenium | 65 mcg |
| | Zinc | 15 mg |
| | Copper | 2 mg |
| Evening Tablet | Calcium Carbonate | 350 mg |
| | B Complex | 110 mg |
| | Vitamin A | 2,000 IU |
| | Folic Acid | 1 mg |
| Evening Capsule | Vitamin E | 400 IU |
| | DHA | 50 mg |
| | Linolenic Acid | 25 mg |
| | Linoleic Acid | 25 mg |
| | Calcium Carbonate | 150 mg |
| Evening Tablet | Alendronate | 10 mg |

It would be anticipated that upon following the above regimen, an average normal menopausal woman would be expected to have reduced incidence of nutritional deficiency and reduced menopausal-related symptoms or disorders when compared to an average normal menopausal woman following a conventional nutritional regimen.

Example 5

The following compositions are for administration to premenopausal women and menopausal women in accordance with the regimen indicated below:

| Regimen | Component | Dose |
| --- | --- | --- |
| First Morning Tablet (orange): | Calcium Carbonate | 350 mg |
| | B Complex | 55 mg |
| Second Morning Tablet (white): | Calcium Carbonate | 350 mg |
| | Vitamin A | 3,000 IU |
| | Vitamin C | 100 IU |
| | Vitamin D | 400 IU |
| | Selenium | 65 mcg |
| | Zinc | 15 mg |
| | Copper | 2 mg |

-continued

| Regimen | Component | Dose |
| --- | --- | --- |
| Evening Tablet | Calcium Carbonate | 350 mg |
| | B Complex | 110 mg |
| | Vitamin A | 2,000 IU |
| | Folic Acid | 1 mg |
| Evening Capsule | Vitamin E | 400 IU |
| | DHA | 50 mg |
| | Linolenic Acid | 25 mg |
| | Linoleic Acid | 25 mg |
| | Calcium Carbonate | 150 mg |
| Evening Tablet | PREMPRO ™ | 2.5 mg |
| | conjugated estrogens progesterone | 2.5 mg |

It would be anticipated that upon following the above regimen, an average normal menopausal woman would be expected to have reduced incidence of nutritional deficiency and reduced menopausal-related symptoms or disorders when compared to an average normal menopausal woman following a conventional nutritional regimen.

The inventive subject matter being thus described, it will be apparent that the same may be varied in many ways. Such variations are not to be regarded as a departure from the spirit and scope of the inventive subject matter, and all such modifications are intended to be within the scope of the appended claims.

We claim:

1. A composition for administration to a menopausal woman, which comprises:
    a first fatty acid compound selected from the group consisting of a linoleic acid compound, a derivative thereof and a combination thereof in an amount of about 10 mg to about 1,000 mg;
    a second fatty acid compound selected from the group consisting of a linolenic acid compound, a derivative thereof and combinations thereof in an amount of about 10 mg to about 1,000 mg;
    a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;
    a calcium compound or derivative thereof in an amount of about 400 mg to about 2500 mg;
    a folic acid compound or derivative thereof in an amount of about 0.4 mg to about 5.0 mg;
    a vitamin C compound or derivative thereof in an amount of about 25 mg to about 500 mg;
    a vitamin E compound or derivative thereof in an amount of about 10 mg to about 500 mg;
    wherein the weight ratio of the sum of the amounts of said first and second fatty acid compounds to the amount of said third fatty acid compound is about 1:0.5 to 1.5; and
    wherein the weight ratio of the sum of the amounts of said first, second and third fatty acid compounds to the amount of said calcium compound or derivative thereof is about 1:0.4 to 50.

2. The composition of claim 1, wherein said composition additionally contains a non-nutritional active.

3. The composition of claim 2, wherein the non-nutritional active is selected from the group consisting of hormones, steroids, fiber, estrogens, progestins, sedative-hypnotics, barbiturates, benzodiazepines, antidepressants, tranquilizers, sedatives, aminobisphosphonates, osteoporotics, herbals, herbal derivatives, phyto-chemical derivatives, antiplatelets and combinations thereof.

4. The composition of claim 2, wherein the non-nutritional active is a hormone, and wherein the hormone is present in said composition in an amount ranging from about 0.15 mg to about 11.25 mg.

5. The composition of claim 2, wherein the non-nutritional active is selected from the group consisting of medroxyprogesterone acetate, megestrol acetate, clonidine, norethindrone acetate, ethinyl estradiol, conjugated estrogen, natural estrogen, synthetic estrogen, estradiol, progesterone, clomiphene, clomiphene citrate, zuclomiphene, zuclomiphene citrate, enclomiphene, enclomiphene citrate, calcitonin, aspirin, alendronate, etidronate, pamidronate, clodronate, tiludronate, residronate, ibandronate and combinations thereof.

6. The composition of claim 2, wherein the non-nutritional active is an osteoporotic, and wherein the osteoporotic is present in said composition in an amount ranging from about 2.5 mg to about 60 mg.

7. The composition of claim 1, wherein the composition additionally contains an amino acid compound or derivative thereof.

8. The composition of claim 7, wherein the amino acid compound is selected from the group consisting of leucine, isoleucine, valine and combinations thereof.

9. A composition for administration to a menopausal woman, which comprises:

a first fatty acid compound selected from the group consisting of a linoleic acid compound, a derivative thereof and a combination thereof in an amount of about 10 mg to about 1,000 mg;

a second fatty acid compound selected from the group consisting of a linolenic acid compound, a derivative thereof and combinations thereof in an amount of about 10 mg to about 1,000 mg;

a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;

a calcium compound or derivative thereof in an amount of about 400 mg to about 2500 mg;

a folic acid compound or derivative thereof in an amount of about 0.4 mg to about 5.0 mg;

a vitamin C compound or derivative thereof in an amount of about 25 mg to about 500 mg;

a vitamin E compound or derivative thereof in an amount of about 10 mg to about 500 mg;

a vitamin A compound or derivative thereof in an amount of about 2,500 IU to about 6,500 IU;

wherein the weight ratio of the sum of the amounts of said first and second fatty acid compounds to the amount of said third fatty acid compound is about 1:0.5 to 1.5; and wherein the weight ratio of the sum of said first, second and third fatty acid compounds to the amount of said calcium compound or derivative thereof is about 1:0.4 to 50.

10. A composition for administration to a menopausal woman, which comprises:

a first fatty acid compound selected from the group consisting of a linoleic acid compound, a derivative thereof and a combination thereof in an amount of about 10 mg to about 1,000 mg;

a second fatty acid compound selected from the group consisting of a linolenic acid compound, a derivative thereof and combinations thereof in an amount of about 10 mg to about 1,000 mg;

a third fatty acid compound selected from the group consisting of a docosahexaenoic acid compound, an omega-3 fatty acid, an omega-2 fatty acid, a derivative thereof and a combination thereof in an amount of about 10 mg to about 1,000 mg;

a calcium compound or derivative thereof in an amount of about 400 mg to about 2500 mg;

a folic acid compound or derivative thereof in an amount of about 0.4 mg to about 5.0 mg;

a vitamin C compound or ester derivative thereof in an amount of about 25 mg to about 500 mg;

a vitamin E compound or derivative thereof in an amount of about 10 mg to about 500 mg;

a vitamin B6 compound or derivative thereof in an amount of about 10 mg to about 50 mg;

a vitamin B12 compound or derivative thereof in an amount of about 25 mcg to about 75 mcg;

a vitamin D compound or derivative thereof in an amount of about 200 IU to about 625 IU;

wherein the weight ratio of the sum of the amounts of said first and second fatty acid compounds to the amount of said third fatty acid compound is about 1:0.5 to 1.5; and wherein the weight ratio of the sum of the amounts of said first, second and third fatty acid compounds to the amount of said calcium compound or derivative thereof is about 1:0.4 to 50.

* * * * *